(12) United States Patent
Doverbo et al.

(10) Patent No.: US 11,213,438 B2
(45) Date of Patent: Jan. 4, 2022

(54) DISPOSABLE WEARABLE ABSORBENT ARTICLE

(71) Applicant: Essity Hygiene and Health Aktiebolag, Gothenburg (SE)

(72) Inventors: Anna-Gerd Doverbo, Mölndal (SE); Verica Terentic, Gothenburg (SE); Henrik Carlén, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/265,297

(22) PCT Filed: Aug. 29, 2018

(86) PCT No.: PCT/EP2018/073270
§ 371 (c)(1),
(2) Date: Feb. 2, 2021

(87) PCT Pub. No.: WO2020/043286
PCT Pub. Date: Mar. 5, 2020

(65) Prior Publication Data
US 2021/0298968 A1    Sep. 30, 2021

(51) Int. Cl.
*A61F 13/15* (2006.01)
*A61F 13/49* (2006.01)
*A61F 13/56* (2006.01)

(52) U.S. Cl.
CPC .... *A61F 13/5622* (2013.01); *A61F 13/15756* (2013.01); *A61F 13/49014* (2013.01)

(58) Field of Classification Search
CPC ............ A61F 13/5622; A61F 13/15756; A61F 13/49014
See application file for complete search history.

(56) References Cited

U.S. PATENT DOCUMENTS

| | | |
|---|---|---|
| 2003/0083635 A1 | 5/2003 | Gibbs |
| 2003/0109843 A1 | 6/2003 | Gibbs |
| 2004/0044324 A1 | 3/2004 | Swenson et al. |
| 2004/0236303 A1 | 11/2004 | Igaue et al. |
| 2005/0215972 A1 | 9/2005 | Roe et al. |
| 2006/0068168 A1 | 3/2006 | Olson et al. |
| 2007/0073260 A1 | 3/2007 | Roe |
| 2008/0208152 A1 | 8/2008 | Eckstein et al. |

FOREIGN PATENT DOCUMENTS

| | | |
|---|---|---|
| CN | 1678272 A | 10/2005 |
| CN | 1937931 A | 3/2007 |
| CN | 101031264 A | 9/2007 |
| JP | 2012239555 A | 12/2012 |
| WO | 2007071268 A1 | 6/2007 |
| WO | 2010/110701 A1 * | 9/2010 |

OTHER PUBLICATIONS

International Search Report (PCT/ISA/210) dated Jun. 4, 2019, by the European Patent Office as the International Searching Authority for International Application No. PCT/EP2018/073270.
Written Opinion (PCT/ISA/237) dated Jun. 4, 2019, by the European Patent Office as the International Searching Authority for International Application No. PCT/EP2018/073270.
First Office Action dated Jul. 26, 2021, by the Chinese Patent Office in corresponding Chinese Patent Application No. 201880096939.9, and an English Translation of the Office Action. (17 pages).

* cited by examiner

*Primary Examiner* — Alma Pipic
(74) *Attorney, Agent, or Firm* — Buchanan Ingersoll & Rooney PC (57) ABSTRACT

A disposable wearable absorbent article comprises a chassis having an absorbent core and first and second side panels extending transversally outwards towards respective outer edges. Each of the first and second side panels comprises a mechanical fastening material affixed to an outer end portion of the panel whereby, in use, the first and second side panels can extend around a user's waist to couple the first and second side panels to the chassis. Each of the side panels is gathered in a longitudinal direction to form at least one pleat extending in the transverse direction, and comprises a binding material affixed to respective side panels to maintain each of the first and second side panels in a gathered configuration. A method for forming disposable wearable absorbent articles is also disclosed.

33 Claims, 5 Drawing Sheets

DISPOSABLE WEARABLE ABSORBENT ARTICLE

TECHNICAL FIELD

The disclosure relates to a disposable wearable absorbent article comprising a chassis having an absorbent core and first and second side panels affixed the chassis, which are configured to extend around the waist of a wearer to secure the article in place.

BACKGROUND

Disposable absorbent articles for absorbing body exudate can take a number of different forms, including insert pads configured to be placed within the underwear, pull-up type briefs and open absorbent articles that are applied in an open configuration and secured around the waist with fasteners to provide a removable diaper or brief-like article.

Open absorbent articles generally comprise a main body or chassis having an absorbent core and at least two side panels or wings that are configured to extend around the user's waist to secure the article in place. Advantages of open absorbent articles include ease of use for wearers and caregivers, flexible and adjustable sizing, ease of manufacture, and high absorbency.

U.S. Patent Application Publication No. US2008/0208152 A1 describes an absorbent incontinence product comprising an absorbent chassis and rectangular front and rear panels configured to fasten to each other around the wearer's waist.

U.S. Patent Application Publication No. US2004/0236303 A1 describes a disposable diaper comprising an absorbent core and front and rear side panels cut to an ergonomic shape for fastening to each other to secure the diaper around the wearer's waist.

U.S. Patent Application Publication No. US2003/0083635 A1 describes a disposable diaper comprising a generally-T shaped chassis and elastomeric fastening tabs for securing the diaper around the wearer's waist.

SUMMARY

In a first aspect, there is provided a disposable wearable article comprising a chassis extending in a longitudinal direction and having a front region, a rear region and a central region disposed in the longitudinal direction between the front region and the rear region. The chassis comprises an absorbent core, advantageously in the central region. A first side panel is connected to the chassis and extends transversally outwards in a first lateral direction towards a first outer edge. A second side panel extends transversally outwards in a second lateral direction towards a second outer edge. The first and second side panels may be attached to the rear region of the chassis. Preferably, the first and second side panels are attached to opposing lateral edges of the rear region of the chassis.

Each of the first and second side panels comprises a mechanical fastening material affixed to a free end portion of the panel adjacent the outer edge of the panel. The first and second panels are configured such that, in use, the first and second side panels can extend around a user's waist to couple the first and second side panels to the front region of the chassis to form a diaper-type article. The end portion of each of the first and second panels is gathered in a longitudinal direction. To maintain each of the first and second panels in a gathered configuration, the panels each comprise a binding material affixed to the end portion of respective side panels. Advantageously, the gathered region of the first and second side panels comprises at least one pleat extending transversely along the respective side panel. The mechanical fastening material can be e.g., one or more hook patches, configured to engage the material of the chassis.

Gathered side panels according to the first aspect can provide varied advantages. For example, by gathering a free end portion of the side panel, a tapered side panel can be formed from a rectangular sheet of material. This may advantageously provide a side panel with improved fit and handleability, starting from a rectangular sheet, which provides manufacturing benefits as further detailed below.

Moreover, additionally or alternatively, gathered side panels according to the present disclosure can increase the ease of use of folded articles, by making the free end of the side panels easier to find and by decreasing the surface area of the side panels that fastens to the mechanical fastening means when the articles are stored in a folded configuration.

Each of the side panels has a width measured in the transverse direction. The transverse direction is perpendicular to or substantially perpendicular to the longitudinal axis of the chassis. Each of the side panels also has a height, which is measured in a direction parallel to or substantially parallel to the longitudinal axis of the chassis.

Preferably, the pleat extends only partially along the transverse width of each side panel such that the panel is ungathered, i.e., comprises no pleats or folds, at the point of attachment with the chassis. This may provide a more comfortable fit and decrease the visibility of the article beneath clothing.

Optionally, the mechanical fastening means acts as the binding material to maintain the first and second side panels in the gathered configuration. This can advantageously reduce material use and simplify the production process.

In some examples, the first and second side panels can be provided as separate sheets, each affixed to the rear portion of the chassis and extending outwardly therefrom. In alternative embodiments, the first and second side panels can be provided as a continuous sheet of material, extending outwardly on either side of the chassis. The side panels may be formed of a sheet having a single layer or a multi-layer sheet, e.g., a laminate of multiple sheets.

The side panels may each be gathered to form a tapered side panel, e.g., a side panel that has a first height measured in a longitudinal direction at its outer edge, and a second height measured in a longitudinal direction at a position laterally inwards of its outer edge, wherein second height is greater than the first height. The second height can be measured at the position at which the side panel is attached to the chassis.

The first and second side panels each comprises a chassis end region, an outer end region and a middle region disposed between chassis end region and the free end region. Advantageously, at least the free end region is made of a substantially non-elastic material. The fastening material and/or the binding material can be affixed to the side panel in the free end region.

In some examples, each side panel can be formed of a continuous sheet of material throughout. In further examples, the middle region can comprise an elastic material. Advantageously, the elastic material can be configured to stretch in at least a transverse direction so that the waist region of the article when worn is elasticated.

Advantageously, at least one of the first and second side panels is formed from a rectangular sheet of material. By forming the first and second side panels of a rectangular sheet of material, material wastage and off-cuts resulting from irregular shaped sheets can be avoided and manufacturing can be simplified. Rectangular sheets of material can comprise a laminate of multiple layers or a single layer.

Advantageously, the binding material extends in a longitudinal direction at or near or adjacent to the outer edge of the side panel, in the free end region. The binding material can be elastic or substantially non-elastic. Where the binding material is elastic, the side panel adopts its gathered configuration with the elastic in its relaxed state. By providing an elastic binding material, the height of the side panel at the outer edge can be adjusted to better fit the wearer.

The elastic material can be used to form the at least one pleat and maintain the side panel in the gathered configuration. For example, the elastic binding material may be stretchable in a longitudinal direction from a contracted, relaxed state to an extended configuration. The elastic binding material can be secured to a respective side panel in its extended configuration and released to form the at least one transverse pleat. Alternatively, the gather can be formed before the binding material is attached to the side panel.

Advantageously, the side panels comprises a gathered region of material adjacent to and laterally inwards of the fastening material. In other words, the at least one pleat formed by the gathering is adjacent to the fastening material, and extending transversely therefrom. In many applications, the free outer ends of the side panels, which carry the fastening material, may be folded over towards the chassis so that the fastening material fastens to the fabric of the side panel immediately adjacent to and laterally inwards of the fastening material. By providing a gathered region of material comprising at least one pleat in this region, the surface area of the side panel that comes into contact with the fastening material when folded over is reduced, thereby making the free ends bearing the fastening material easier to unfold.

In some examples, at least one of the binding material and/or the mechanical fastening material is disposed entirely within a perimeter of the side panel. In alternative examples, the mechanical fastening material and/or binding material may extend beyond the outer edge. In examples in which the fastening material and binding material are separate components, the mechanical fastening material can overlie the binding material.

Generally, the disposable wearable absorbent article comprises a body-oriented surface facing the user during use and a garment-oriented surface facing away from the user during use. In some examples, the mechanical fastening material is provided on the body oriented surface of the side panels and is configured to engage the garment oriented surface of the article, in the front region of the chassis.

It will be understood that the mechanical fastening material and/or the binding material can be provided in the form of a continuous strip of material or a plurality of discrete fastening material regions.

In addition to the gathered side panels, the mechanical fastening material can also be gathered in the longitudinal direction. This can further increase the ease with which the user can find the fastener at the free end of the panel and further decreases the force required to unfasten the fastener from the adjacent material.

In examples comprising an elastic binding and/or fastening material, the first and second side panels can retain their elasticity or they can be fixed in the gathered configuration with a non-elastic material secured to the outer edge of the side panels, with the elastic material in the retracted configuration.

Optionally, the outer edge of each side panel is folded over towards the chassis such that the mechanical fastening material fastens to a surface of the side panel. Advantageously, in the folded configuration, the fastening material overlies the gathered region.

In some examples with tapered side panels, the side panel can have a height $H_2$ at a chassis end measured in a longitudinal direction. At the free outer edge of the side panel, the panel can have a height $H_1$ in the gathered configuration. Preferably, the first height $H_1$ is less than the second height $H_2$.

In some examples, the gathered height $H_1$ can be between 50 to 95% of a third height $H_3$, which is the ungathered outer edge of the respective side, i.e., the height of the free end of the sheet that forms the side panel before it has been secured in its gathered position. In examples in which the side panels are formed of a rectangular sheet of material, the outer edge height $H_1$ and the ungathered height $H_3$ are equal. The gathered height $H_1$ can therefore be 50-95% of $H_2$.

In some examples, the disposable wearable article can comprise third and fourth side panels extending laterally from the front region of the chassis towards third and fourth outer edges respectively. In such examples, the mechanical fastening material on the first and second side panels can be configured to engage the front region of the chassis and/or the third and fourth side panels respectively or the front region of the chassis.

In a second aspect, there is provided a method of manufacturing a disposable wearable absorbent article comprising a chassis and first and second gathered side panels. The method comprises: providing a chassis extending in a longitudinal direction and having a front region, a rear region and a central region disposed in the longitudinal direction between the front region and the rear region; affixing a first side panel to the chassis such that the first side panel extends transversally outwards in the first lateral direction towards a first outer edge; affixing a second side panel to the chassis such that the second side panel extends transversally outwards in a second lateral direction towards a second panel outer edge; gathering each of the first and second side panels in a longitudinal direction to form at least one pleat extending in the transverse direction. The above steps can be carried out any particular order or may preferably be carried out in sequence. The manufacturing process advantageously further comprises the step of applying a binding material to maintain each of the side panels in the gathered configuration. The binding material can be applied before, during or after the step of gathering the first and second side panels. Usefully, the binding material is affixed to the first and second side panels in free end region adjacent the outer edge of the panel.

In some examples, the binding material is an elastic material and the step of gathering the outer edge of each side panel comprises: extending a first length of elastic material in the longitudinal direction to an extended configuration and securing the elastic material, in the extended configuration, at the outer edge of the first side panel in the longitudinal direction; extending a second length of elastic material in the longitudinal direction to an extended configuration and securing the elastic material, in the extended configuration, at the outer edge of the second side panel in the longitudinal direction; relaxing the elastic material to gather each of the first and second side panels in the longitudinal direction.

In alternative examples, the step of gathering the outer edge of each of the side panels can comprise the steps of: gathering the outer edge of each of the respective side panels; applying a binding material to maintain the outer edge of each of the respective side panels in a gathered configuration. In such examples, the binding material can be elastic or substantially non-elastic.

Methods according to the disclosure can further comprises affixing a mechanical fastening material to the outer edge of the side panels. This step can be carried out before attaching the binding material, before attaching the binding material or at the same time as attaching the binding material. In some examples, the binding material can comprise the mechanical fastening material. Elastic and non-elastic mechanical fastening materials can act as the binding material.

In some examples, the method can further comprise the step of folding the outer edge of each side panel over towards the chassis to temporarily fasten the mechanical fastening material to a gathered surface of the side panel.

Advantageously, the first and second side panels can be formed of at least one rectangular sheet of material.

BRIEF DESCRIPTION OF THE DRAWINGS

The disclosure will now be described in more detail with reference to the exemplary articles shown the following drawings, in which.

DETAILED DESCRIPTION OF THE DRAWINGS

The present disclosure relates generally to disposable hygiene articles and more specifically to wearable disposable absorbent articles for management of incontinence.

In the context of the present disclosure, "wearable" is intended to relate to articles that are supported on the body of the wearer without the need for additional products to hold the articles in place. For example, a disposable wearable absorbent article within the meaning of the present disclosure is intended to cover diapers and brief-like articles that can be worn under clothing in place of or in addition to underwear.

In the context of the present disclosure, "disposable" is used in its ordinary sense to mean an article that is disposed of or discarded after a limited number of usage events and/or over varying lengths of time. For example, for the disposable articles described in the present disclosure, the article can be intended to be disposed of after fewer than 10 events, fewer than 5 events, or after 1 event.

Parts of the article described herein may be formed of a non-woven material. In the context of the present disclosure, a "non-woven" material is a manufactured sheet, web or batt of directionally or randomly oriented fibres, bonded by friction, and/or cohesion and/or adhesion, excluding paper and products which are woven, knitted, tufted, stitch-bonded incorporating binding yarns or filaments, or felted by wet-milling, whether or not additionally needled. The fibres may be of natural or man-made origin and may be staple or continuous filaments or be formed in situ. Commercially available fibres have diameters ranging from less than about 0.001 mm to more than about 0.2 mm and they come in several different forms: short fibres (known as staple, or chopped), continuous single fibres (filaments or monofilaments), untwisted bundles of continuous filaments (tow), and twisted bundles of continuous filaments (yarn). Non-woven materials can be formed by many processes such as meltblowing, spunbonding, solvent spinning, electrospinning, and carding.

The following detailed description is made with reference to a number of exemplary configurations. The exemplary configurations provide examples of how the invention may be carried out. However, the invention is not limited to the exemplary configurations set forth herewith and modifications can be made without departing from the scope of the invention.

Figure 1:
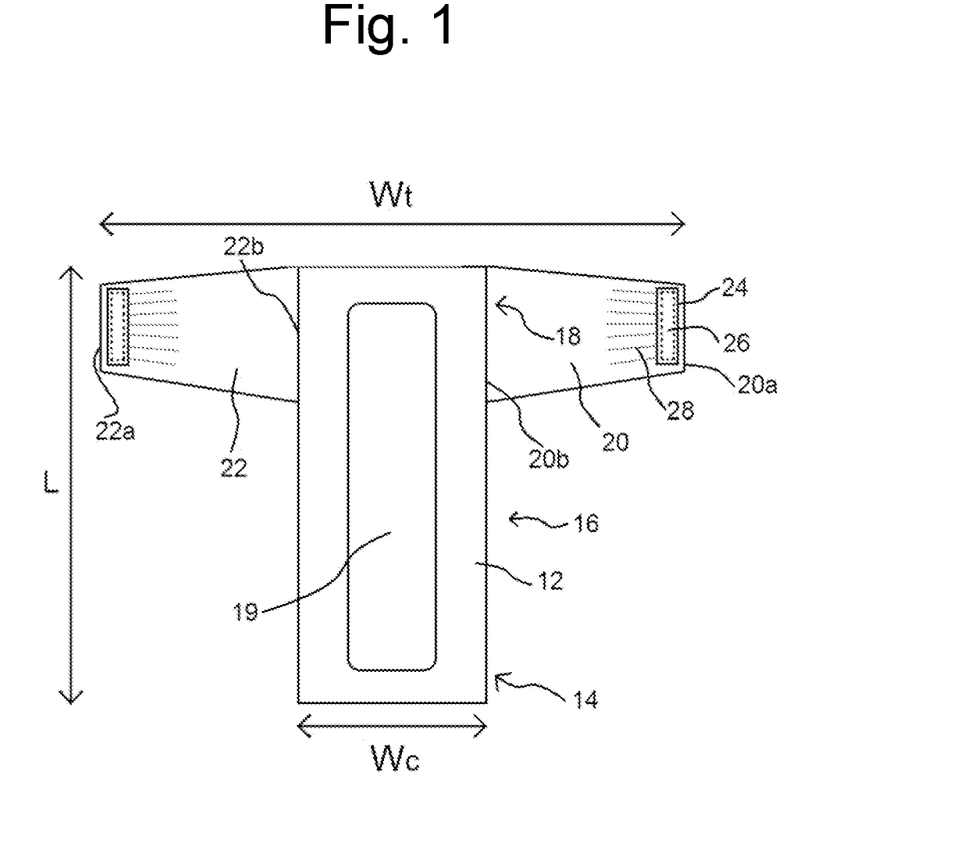
FIG. 1 shows a plan view of a first exemplary disposable wearable absorbent article comprising a chassis having an absorbent core and first and second gathered side panels.

FIG. 1 shows a disposable hygiene product in the form of a disposable wearable absorbent article 10. The absorbent article 10 is of the open type and comprises a chassis 12 having a front region 14, a central region 16 and a rear region 18. The chassis 12 extends from the front region 14 to the rear region 18 in a longitudinal direction. The middle region 16 is disposed between the front region 14 and the rear region 18 in the longitudinal direction. An absorbent core 19 is provided in the chassis, and occupies at least a portion of the central region. During use, the central region 16 is configured to be positioned in a crotch region of the wearer, with the front region 14 pulled up towards the belly, and the rear region 18 partially covering the buttocks.

The article 10 comprises side panels 20, 22 that extend transversally outwards from the chassis 12 to pass around a wearer's waist and/or hips. The side panels 20, 22 each comprise an attachment end portion, adjacent to the chassis 12 and a free end portion, at the opposite end to the attachment portion. The side panels 20, 22 are dimensioned to allow the free ends thereof to be secured to the front region 14 of the chassis to form a brief-like fit for the wearer. By "transversally outwards" it is meant that the first and second side panels extend away from a central longitudinal axis of the chassis 12. As shown in FIG. 1, the first side panel 20 extends in a first lateral direction away from the chassis 12 towards a free end having a first outer edge 20a. The second side panel 22 extends in a second lateral direction, away from the chassis 12 towards a free end having a second outer edge 22a. The first and second side panels 20, 22 are attached to the chassis 12 at respective attachment edges 20b, 22b.

In the example shown in FIG. 1, the side panels 20, 22 are formed of separate sheets and attached to lateral edges of the chassis 12. The skilled person will appreciate that other means of attachment of the side panels 20, 22 are possible. For example, the side panels 20, 22 may be formed of a continuous sheet of material that extends in front of or behind the rear region 18 of the chassis 12. In such examples, the continuous sheet of material can be secured to the chassis at the lateral edge of the chassis 12. In yet further examples, the side panels 20, 22 may be formed of a continuous sheet of material that extends in a transverse direction, abutting an end edge of the chassis 12. In such examples, the continuous sheet of material can be secured to the chassis along a top edge of the rear region 18. In all cases, it will be understood that the chassis 12 together with the first and second side panels 20, 22 form a substantially T-shaped body, as shown in FIG. 1.

A mechanical fastening material 24 is affixed to an end portion of each side panel 20, 22. In the example shown in FIG. 1, the fastening material 24 is affixed to the side panel 20 laterally inwards of and adjacent to the free end edge 20a. However, the skilled person will appreciate that the mechanical fastening material 24 can extend beyond the free end edge 20a. The mechanical fastening material 24 is configured to fasten the end portions of the side panels 20, 22 to the front region 14 of the chassis 12. The mechanical fastening material 24 can be a hook patch, configured to engage the chassis 12, e.g., a hook patch configured to engage a non-woven material, from which the outer surface of the chassis 12 can be formed, or a loop material patch disposed on the outer surface of the chassis. The materials used to form the chassis and side panels will be discussed in more detail with reference to FIGS. 2 and 3. The fastening material 24 can comprise a continuous length of fastening material, or it can comprise a plurality of discrete sections of fastening material. For example, the fastening material 24 can be provided in the form of a strip (as shown in FIG. 1) or it can comprise a series of discrete spots, strips or other shapes, as will be understood by the person skilled in the art. When combined with an elastic binding material, discrete regions of fastening material 24 can allow the side panel 20, 22 to retain its elasticity in the longitudinal direction, even if the fastening material is substantially non-elastic.

The advantages provided by the present disclosure can be particularly applicable to relatively large sized, adult diapers. To ensure a proper fit for the wearer and appropriate absorbency, the chassis 12 can be generally relatively long and narrow. The longitudinal length L of the article 10 may be from 500 mm, from 600 mm or from 700 mm, to 1200 mm, 1000 m or 800 mm. The length L is measured with the article 10 in a flattened-out state, with any longitudinally or transversely contracting elements in the chassis in a deactivated state, i.e., exerting no contracting force on the chassis, either by virtue of having been removed or severed.

The transverse width $W_c$ of the chassis 12 may be from 150 mm, from 200 mm or from 250, to 400 mm, 350 mm, or 300 mm. The width of the chassis can be constant along its length. Alternatively, the chassis 12 can be hourglass shaped. Preferably, the width of the chassis 12 should be chosen such that the central region 16 can be comfortably placed in the crotch region, between the wearer's legs.

The transverse width $W_t$ of the article 10, from the first outer edge 20a to the second outer edge 22a can be from 500 mm, from 600 mm, or from 700 mm, to 1200 mm, 1000 mm, or 800 mm. In some examples, the transverse width $W_t$ of the article 10 is equal to the longitudinal length L of the chassis 12, +/−20% (as measured in the flattened out state). This ratio of total width $W_t$ to chassis length L generally provides articles of an appropriate size and shape for adult wearers.

As shown in FIG. 1, each of the first and second side panels 20, 22 is gathered in a longitudinal direction to form at least one pleat 28 extending substantially in the transverse direction. A binding material 26 is affixed to the end portion of each side panel to maintain the panel 20, 22 in the gathered configuration. The gathered configuration of the side panels 20, 22 will be discussed in more detail with reference to FIGS. 3 to 5.

Figure 2:
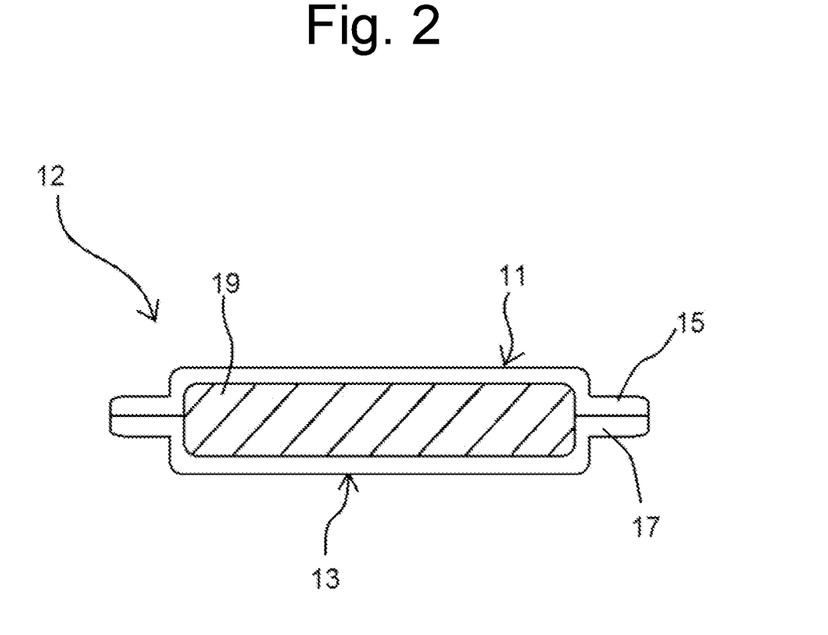
FIG. 2 shows a cross-sectional view of an exemplary chassis comprising an absorbent core.

FIG. 2 shows a cross-section of the chassis 12 in the central region 16. As shown in FIG. 2, the chassis 12 comprises a body facing surface 11 intended to face the body of a wearer during use and a garment facing surface 13 intended to face away from the wearer during use. Generally, the chassis 12 comprises a liquid permeable topsheet 15 at the body facing surface and a liquid impermeable backsheet 17 at the garment facing surface. The absorbent core 19 is arranged between the topsheet 15 and the backsheet 17 and is configured to absorb body exudate, e.g., urine or other bodily fluids.

The absorbent core 19 may be of any type suitable for the type of absorbent article intended, such as, but not limited to a mixture of cellulosic fibers and superabsorbent polymer, essentially cellulose-free absorbent cores, such as comprising 85% or more superabsorbent polymer, and foam-based absorbent cores.

The topsheet 15 is suitably sufficiently fluid permeable to allow discharged body fluids such as urine to penetrate through the thickness of the topsheet 15. Advantageously, the topsheet 15 can be suitably manufactured from a material which is compliant and soft-feeling to the skin of the wearer.

Materials suitable for use as a topsheet 15 are commonly known in the art of disposable hygiene products, and for the purposes of the present disclosure, any material commonly known for use as a topsheet may be used, including, but not limited to non-woven materials and perforated polymeric films. The topsheet 15 may be manufactured from various web materials such as woven and nonwoven webs, perforated films, open cell foams, or combinations or laminates of the above-mentioned materials.

The nonwoven materials to be used for the topsheet 15 may for example be made of a spunbond, a spunbond/spunbond composite, or a spunbond/meltblown composite, such as a SMS (spunbond/meltblown/spunbond), SSMS, SSMMS, SMMS, non-woven material of polypropylene or bicomponent fibres of polypropylene and polyethylene, or of a combination of such materials. The topsheet 15 may also have elastic properties.

The backsheet 17 is suitably impermeable to liquid (such as urine) to prevent leakage of exudate through the backsheet 17. The backsheet 17 prevents the exudates absorbed by the absorbent assembly from soiling other external articles that may contact the disposable absorbent hygiene product, such as bedsheets and undergarments.

Materials suitable for use as a backsheet 17 are also commonly known in the art of disposable hygiene products. For the purposes of the present disclosure, any material commonly known for use as a backsheet may be used, including but not limited to polymeric films, for example films of polyethylene, polypropylene or copolymers of polyethylene or polypropylene, hydrophobized non-woven materials, fluid impermeable foams and fluid impermeable laminates. Preferably, the backsheet is substantially liquid impermeable but breathable, i.e., gas permeable, implying that air and other gases may pass through the backsheet 17, while being substantially impermeable to liquids.

The backsheet 17 may also comprise one or more layers of material. For example, the backsheet may be a laminate of a liquid impermeable polymeric film towards the absorbent assembly and non-woven towards the garment side, to provide a textile, soft feeling to the outer surface of the disposable absorbent hygiene product.

As shown in FIG. 2, the topsheet 15 and the backsheet 17 may extend outside the outer contour of the absorbent core 19 and be joined together outside the absorbent core contour using methods commonly known in the art, such as gluing or welding by means of heat or ultrasound.

Elastic means (not shown) that extend in a generally longitudinal manner may be attached to the main part of chassis 12, for example, sandwiched between the topsheet and the backsheet close to the longitudinal side edges for providing leg cuffs, as is commonly known in the art. Such elastic means may comprise one or more elastic threads, elastic film strips, or elastic foam strips, and may be attached to the chassis 12 in a stretched state in order to exert a longitudinally contracting force on the disposable absorbent article 10.

Figure 4:
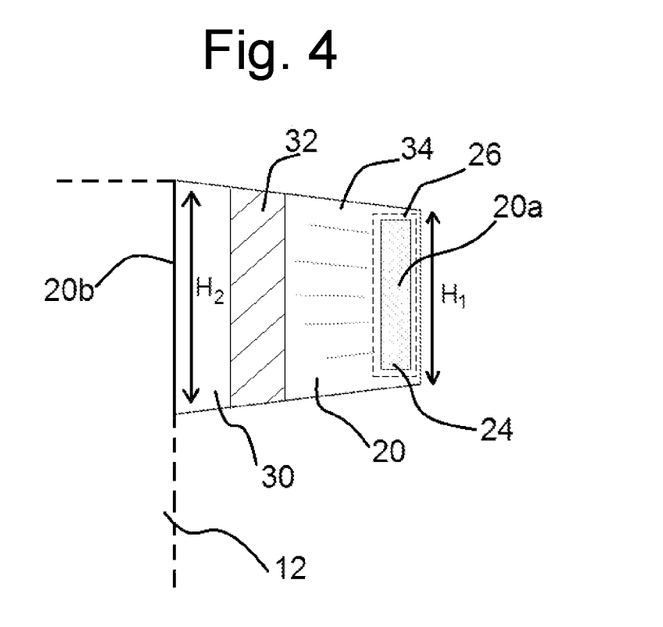
FIG. 4 shows a second configuration for an exemplary gathered side panel.
Figure 5:
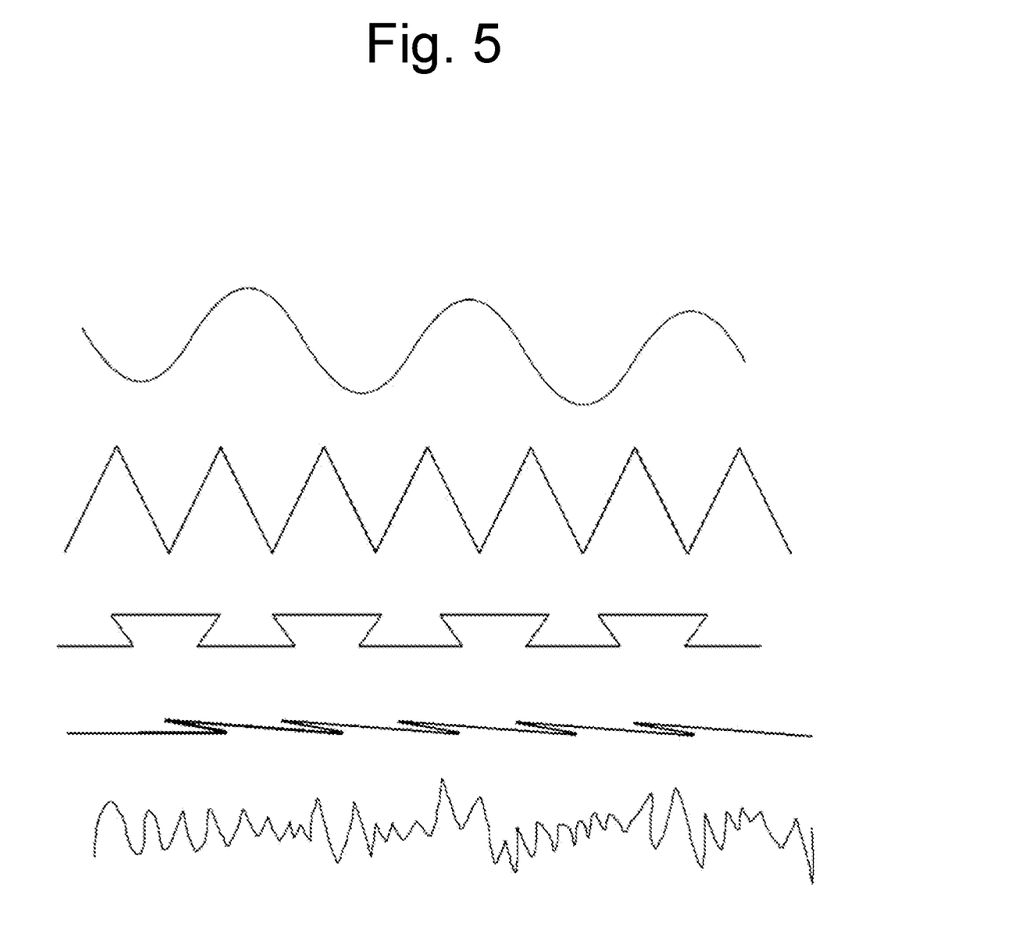
FIG. 5 shows a cross-sectional view of five exemplary gathered side panels.

The gathered side panels will now be discussed further with reference to FIGS. 3 to 5.

Figure 3:
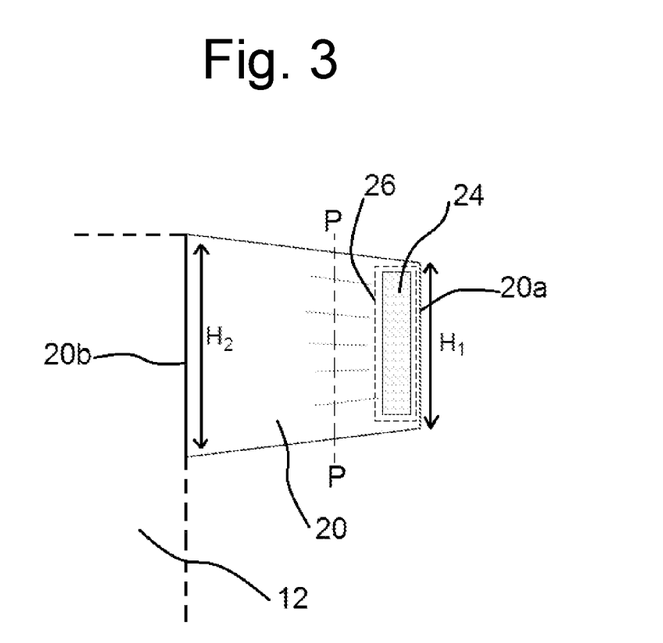
FIG. 3 shows a first configuration for an exemplary gathered side panel.

FIG. 3 shows a side panel 20 from FIG. 1 in more detail. Side panel 22 has a similar configuration. As shown in FIG. 3, side panel 20 comprises a free outer edge 20*a* and an attachment edge 20*b*. The panel 20 is secured to the chassis 12 at or near the attachment edge 20*b*. The panel 20 is arranged such that it extends in a first lateral direction away from the chassis 12 towards the free outer edge 20*a*. The panel 20 can be considered to have three portions: an outer end portion adjacent and laterally inward of the free outer edge 20*a*; an attachment end portion adjacent to and laterally outward of the attachment edge 20*b*; and a middle portion disposed between the end portions. As shown in FIG. 3, the side panel 20 can comprise a continuous sheet of material. The sheet of material that forms the side panel 20 can comprise a substantially non-elastic material. For example, the side panel 20 can be formed of a sheet of non-woven material.

In some examples, the side panel can comprise a sheet formed of multiple pieces of material, joined to each other to form a side panel sheet. For example, as shown in FIG. 4, the side panel 20 can comprise a first non-elastic section 30 immediately adjacent the attachment edge 20*b*. An elastic section 32 is joined to the first non-elastic section 30 at its first edge. At its second edge, the elastic section 32 is joined to a second non-elastic section 34. The first and second non-elastic sections 30, 34 can comprise a non-woven material. The elastic section 32 is preferably extendable in at least a transverse direction. Transversely elastic or elasticized portions of the side panels may be made from any material suitable for use as side panels in disposable absorbent articles. For example, elastic materials, such as elastic films, elastic non-wovens, or elastic laminates can be joined to non-elastic regions of the side panels by joining methods commonly known in the art, such as gluing, thermo-welding or ultrasonic welding. Examples of elastic laminates include for example nonwoven-film laminates comprising at least one layer of nonwoven joined to an elastomeric material, such as an elastomeric film or a plurality of elastic threads, such as spandex threads, and include laminates commonly known as stretch bond laminates and laminates activated by ring-rolling, such as for example disclosed in EP 0 650 714. Preferably, at least the outer end portion of the side panel 20, adjacent the free end edge 20*a* is substantially non-elastic.

The fastening material 24 is provided in the outer end region, at or adjacent the free outer edge 20*a* of the panel 20. The fastening material 24 can comprise a mechanical fastening material 24, such as one or more hook patches. Fastening materials, such as hook patches configured to engage and fasten to, for example, non-woven materials commonly used in disposable absorbent articles are known in the art and can be chosen by the person skilled in the art in combination with the materials used for the chassis 12 and side panels 20, 22. The fastening material 24 can be elastic (e.g., extendable in the longitudinal direction) or it can be substantially non-elastic.

The binding material 26 extends in substantially longitudinal direction in the outer end portion of the panel 20, preferably at or adjacent to the free outer edge 20*a*. The longitudinal direction is the direction substantially parallel to the longitudinal axis of the chassis 12. The binding material 26 is configured to maintain at least part of the side panel 20 in the gathered configuration. The binding material 26 is configured to maintain the outer end portion in the gathered configuration in a rest position, e.g., when no external force is applied to stretch the binding material.

By a gathered configuration it is meant a configuration in which a region of material that forms the side panel 20 is gathered, ruched, wrinkled or folded to form at least one pleat 28. Within the context of the present disclosure, the at least one pleat can comprise a barrel pleat with an undulating cross-section, a folded region, or the like. At least one pleat 28 is formed in the gathered region, however, advantageously a plurality of pleats are formed, e.g., at least three pleats, alternatively at least 10 pleats, alternatively at least 20 pleats. The at least one pleat 28 extends in a transverse direction, from the binding material 26 substantially towards the chassis 12. The at least one pleat 28 provides a non-planar surface at or near the free end edge of the side panel 20, preferably adjacent to and laterally inward of the fastening material 24. Within the context of the present disclosure, the presence of at least one pleat is judged with the article 10 in a flattened-out state on a flat surface, with any contracting elastic elements in the chassis 12 deactivated and with any contracting elements in the side panels (e.g., an elastic binding material 26) in a naturally contracted state.

The non-planar surface provided by the gathered or wrinkled side panel provides a number of advantages. The at least one pleat 28 provides a textured surface at the free end of the side panel, which may be easier to feel with the finger tips, thereby providing tactile feedback to the user regarding the location of the free end. In many circumstances, adult diapers are supplied with the free ends of the side panels folded over, such as folded along a folding line close to and transversally inwards of the fastening material, with the fastening material engaging the non-woven material of the side panel. Unfolding the free ends can be difficult when the fastening material is securely attached to the side panel material. A gathered region, as described above, can improve the ease with which the free ends can be unfolded because the gathered or wrinkled surface can allow the user to more easily grip or grasp the free end. Moreover, the uneven surface of the gathered region decreases the surface area of the side panel in contact with the fastening material, thus making it easier to unfasten.

The skilled person will appreciate that the precise configuration of the at least one pleat 28 and the resulting gather can be varied. FIG. 5 shows five possible cross-sections of the gathered region of the side panel 20, along line P-P, as shown in FIG. 3. As shown in FIG. 5, the pleats 28 of the gathered region can take multiple forms and the skilled person will appreciate that other pleat configurations are possible. The pleats can be regular or irregular. For example, the at least one pleat 28 can be formed as a barrel pleat having an approximately undulating or sinusoidal cross-section. The pleats can be formed by sharp folds, box or knife pleats, or an irregular wrinkled surface.

The gathered region at the outer edge of the side panel 20 can also be used to form a tapered side panel, which tapers towards its free end. As shown in FIGS. 3 and 4, the side panel 20 has a first height $H_1$ at its outer edge 20*a*, when the panel is in the gathered configuration. The first height $H_1$ is measured with the panel 20 flattened-out, with all elastic components in an activated (i.e., naturally contracted) state with no external force extending the elastics. In other words, the first height $H_1$ is measured when no external force is applied to stretch or extend the binding material 26.

At the chassis attachment edge 20b, the panel 20 has a second height $H_2$. The second height $H_2$ is measured in a longitudinal direction (with reference to the chassis 12) with the panel 20 flattened-out, with any elastics in a naturally contracted state. Preferably, the attachment end 20b of the panel 20 is substantially ungathered, i.e., comprises no pleats or folds. As shown in FIGS. 3 and 4, $H_1$ is preferably less than $H_2$, thus giving the side panel 20 a tapered shape. In preferred examples, $H_1$ is between 50% and 95% of $H_2$, more preferably between 60% and 80% of $H_2$. The height of a side panel is measured in the longitudinal direction.

The height $H_2$ of the side panels at the attachment end 20b to the chassis may be in the range of from 100 mm, from 120 mm, from 140 mm, to 240 mm, to 220 mm, to 200 mm or to 180 mm, for example, approximately 160 mm.

In order to provide a comfortable absorbent wearable article, it is preferred that the article, once secured in place, has the look and feel of underwear, such as a pair of briefs. It is thus preferred to configure the side panels of open articles such that they are relatively high at the point of attachment to the chassis to provide good coverage for the buttocks of the wearer. However, the height required for comfortable coverage of the buttocks may be larger than the height preferred for the free ends of the side panels (see ranges above). This is because high side panels at the free end generally provide a less flexible fit and can be difficult to handle because they cannot be held firmly in one hand.

To minimise wastage and simplify the cutting and formation process, it is also generally preferred to cut side panels having a rectangular shape. Therefore, in some examples, the panel 20 may be formed of a substantially rectangular sheet of material. In such examples, the panel 20, before gathering, has a height $H_3$ at its outer edge that is equal to $H_2$, the height at the attachment edge. In preferred examples, $H_1$ is between 50% and 95% of $H_3$, more preferably between 60% and 80% of $H_3$. The skilled person will appreciate that advantages associated with the present disclosure are also applicable to side panels having a non-rectangular starting shape. The present disclosure thus incorporates side panels formed from sheets of material having non-rectangular shapes, e.g., a trapezoidal shape, an irregular shape, or a rounded shape.

By gathering the side panels at the free end, as described above, the shape of the side panel can be modified, without cutting the side panel. For example, a tapered side panel can be provided, from a rectangular sheet of material. This can simplify the manufacturing process in addition to providing the advantages discussed above.

Figure 6:
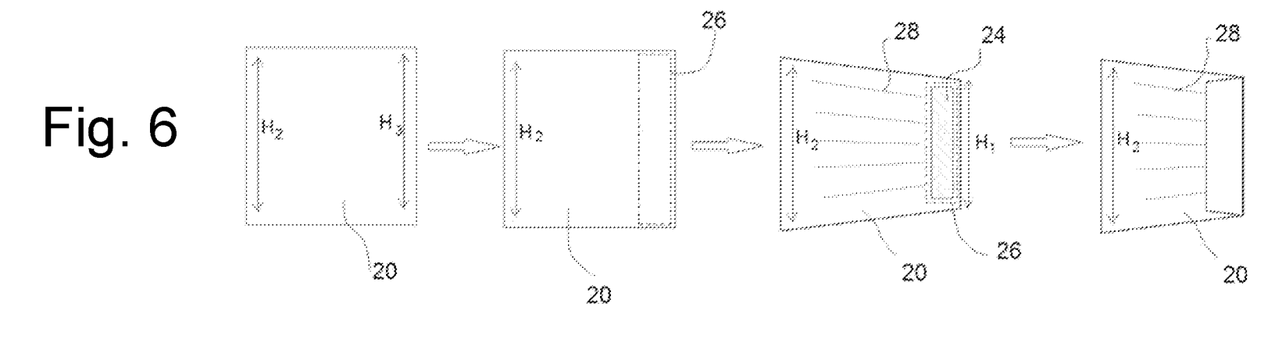
FIG. 6 shows the steps of an exemplary first method for making a gathered side panel.
Figure 7:
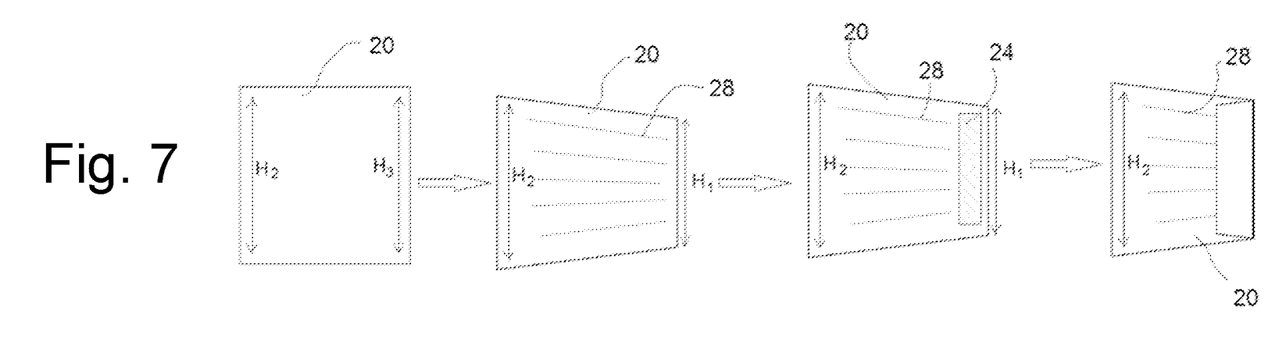
FIG. 7 shows the steps of an alternative exemplary method for making a gathered side panel.

Referring now to FIGS. 6 and 7, the gathering of the side panel can be achieved in various ways. As shown in FIG. 6, the side panel 20 can be cut to have a rectangular shape, where $H_2=H_3$. Starting with the panel 20 in a flattened configuration, the at least one pleat 28 can be formed by applying an elastic binding material 26 in an extended state to the free end portion of the side panel 20. The elastic material is extended from its relaxed state to an extended configuration by placing the elastic material under stretching tension. In the extended state, the elastic binding material 26 is bonded to the side panel 20 using any suitable method known in the art. After the binding material 26 has been bonded to the side panel, the elastic binding material 26 is released and allowed to return to its relaxed, contracted state. The contraction of the elastic binding material 26 acts to gather the free end of the side panel 20. As shown in FIG. 6, the fastening material 24 can be applied to the side panel 20 once the gathered configuration has been achieved. In some examples, the fastening material can also be formed of a substantially elastic material, elastically extendable in the longitudinal direction. In such examples, the free end of the panel 20 can be elastically extendable in the longitudinal direction. This means that the height $H_1$ can be varied according to a user's needs when the free end of the side panel 20 is secured to the front region 14 of the chassis 12. Elastic fastening material 24 can be applied at the same time as the elastic binding material 26 or after the elastic binding material has been allowed to return to its relaxed state. In some examples, the elastic binding material 26 can be provided by the elastic fastening material 24. In this case, the binding material and the fastening material are combined into a single component and dedicated binding and fastening materials are not required.

In other examples, the fastening material 24 can be substantially non-elastic. Non-elastic fastening material 24 can also be applied at the same time as the elastic binding material 26 or after the elastic binding material has returned to its relaxed state. Where a non-elastic fastening material 24 is applied at the same time as an extended elastic binding material 26, the elastic binding material 26 gathers the fastening material 24, as well as the side panel 20, as it returns to its relaxed state. Gathered fastening material can further aid the user to unfold and unfasten the free ends of the side panels 20. Where a non-elastic fastening material 24 is applied after the elastic binding material 26 has been allowed to return to its relaxed state, the fastening material 24 fixedly secures the side panel 20 in its gathered state such that it cannot be adjusted by the user upon fastening.

As an alternative to the gathering method described with reference to FIG. 6, the side panel 20 can be gathered before a binding material 26 is applied. As shown in FIG. 7, the side panel 20 is cut with a rectangular shape, in which $H_2=H_3$. The side panel 20 is then gathered at its free end to create at least one pleat 28 extending in a transverse direction. The panel 20 may be gathered by applying a vacuum between the panel 20 and a corrugated support surface. With the panel 20 in the gathered configuration, a binding material 26 is applied to maintain the panel 20 in the gathered configuration. The binding material 26 may be elastic (e.g., extendable in a longitudinal direction) or it may be substantially inelastic. The advantages of elastic and substantially non-elastic binding materials are explained above. The fastening material 24 (elastic or substantially non-elastic) may be applied as a separate component or may be integrated with the binding material 26. Like the fastening material 24, the binding material 26 can be provided as a continuous length of binding material 26 or a plurality of discrete sections of binding material 26.

Where the fastening material 24 and the binding material are provided as separate components, the fastening material 24 can overlie the binding material 26. In alternative examples, the binding material 26 and the fastening material 24 can also be provided on opposite sides of the side panel 20 or the binding material can be provided in adjacent to the fastening material or in a partially overlapping configuration.

The exemplary methods shown in FIGS. 6 and 7 can further comprise an optional step of folding the outer free end of the side panel laterally inwardly towards the chassis to fasten the fastening material to the side panel in the region of the at least one pleat. Folding the fastening material over in this manner can prevent the fastening material 24 fastening unintentionally to other parts of the wearable disposable article 10. As described above, fastening the fastening material to the gathered region of the side panels 20, 22 can also make the free outer end of the side panel easier to unfasten and unfold.

Although not shown in the drawings, in some examples the disposable wearable absorbent article 10 can further comprise third and fourth side panels extending laterally outwards from the front region 14 of the chassis 12. The third and fourth side panels can comprise a non-woven material and can provide additional sizing flexibility and improved handling for the user. In examples comprising third and fourth side panels, the fastening material 24 on the first and second side panels can be configured to fasten to the garment facing surface 13 in the front region 14 of the chassis 12 or to the garment facing surface of the third and fourth side panels.

The present disclosure has been described with reference to a number of exemplary embodiments. The invention is not limited to the scope of the illustrative embodiments and the skilled person will understand that adaptations and modifications may be made without departing from the scope of the invention.

The invention claimed is:

1. A disposable wearable absorbent article comprising:
   a chassis extending in a longitudinal direction and having a front region, a rear region and a central region disposed in the longitudinal direction between the front region and the rear region, the central region comprising an absorbent core;
   a first side panel connected to the chassis and extending transversally outwards in a first lateral direction towards a first outer edge;
   a second side panel connected to the chassis and extending transversally outwards in a second lateral direction towards a second outer edge;
   wherein each of the first and second side panels comprises a mechanical fastening material affixed to a free end portion adjacent the outer edge of the each of the first and second side panels, whereby, in use, the first and second side panels can extend around a user's waist to couple the first and second side panels to the front region of the chassis, and
   wherein each of the first and second side panels is gathered in a longitudinal direction to form at least one pleat extending in a transverse direction, and
   wherein each of the first and second panels comprises a binding material affixed thereto, the binding material being configured to maintain each of the first and second side panels in a gathered configuration.

2. The disposable wearable absorbent article according to claim 1, wherein the binding material is provided by the mechanical fastening material.

3. The disposable wearable absorbent article according to claim 1, wherein each of the first and second side panels is gathered to form a tapered side panel that has a first height measured in a longitudinal direction at its outer edge and a second height measured in a longitudinal direction at a position laterally inwards of its outer edge, and wherein the second height is greater than the first height.

4. The disposable wearable absorbent article according to claim 1, wherein each of the first and second side panels comprises a chassis end portion and a middle region disposed between the chassis end region and the free end portion, and wherein at least the free end region is formed of a substantially non-elastic material.

5. The disposable wearable absorbent article according to claim 4, wherein the middle region comprises an elastic material, the elastic material being configured to stretch in at least the transverse direction.

6. The disposable wearable absorbent article according to claim 1, wherein at least one of the first and second side panels is formed from a rectangular sheet of material.

7. The disposable wearable absorbent article according to claim 1, wherein the first and second side panels are formed as a continuous piece.

8. The disposable wearable absorbent article according to claim 1, wherein the binding material of each of the first and second side panels respectively extends in the longitudinal direction adjacent to the outer edge of the each of the first and second side panels.

9. The disposable wearable absorbent article according to claim 1, wherein the binding material is substantially non-elastic.

10. The disposable wearable absorbent article according to claim 1, wherein the binding material is an elastic material.

11. The disposable wearable absorbent article according to claim 10, wherein the elastic material is stretchable in the longitudinal direction from a contracted configuration to an extended configuration, and wherein the elastic material is secured to each of the first and second side panels respectively in its extended configuration such that the outer edge of each of the first and second side panels has a longitudinally extended configuration and a longitudinally contracted configuration to form the at least one transverse pleat.

12. The disposable wearable absorbent article according to claim 1, formed by gathering each of the first and second side panels before the binding material is applied.

13. The disposable wearable absorbent article according to claim 1, wherein each of the first and second side panels comprises a gathered region of material adjacent to and laterally inwards of the fastening material.

14. The disposable wearable absorbent article according to claim 1, wherein at least one of the binding material and the mechanical fastening material of the first or second side panel is disposed entirely within a perimeter of the first or second side panel.

15. The disposable wearable absorbent article according to claim 1, wherein the mechanical fastening material overlies the binding material.

16. The disposable wearable absorbent article according to claim 1, comprising a body-oriented surface configured to face the user during use and a garment-oriented surface configured to face away from the user during use, wherein the mechanical fastening material is provided on the body-oriented surface and is configured to engage the garment-oriented surface of the article.

17. The disposable wearable absorbent article according to claim 1, wherein the mechanical fastening material comprises:
    a continuous strip of fastening material; or
    a plurality of discrete fastening material regions.

18. The disposable wearable absorbent article according to claim 1, wherein the mechanical fastening material is gathered in the longitudinal direction.

19. The disposable wearable absorbent article according to claim 10, wherein the first and second side panels are fixed in the gathered configuration with a non-elastic material secured to the outer edge of the each of the first and second side panels with the elastic material in a retracted configuration.

20. The disposable wearable absorbent article according to claim 1, wherein each of the first and second side panels comprises an additional region of elastic material transversally between the chassis and the outer edge of the each of the first and second side panels, wherein the additional region of elastic material is configured to allow the each of the first and second side panels to expand in a transverse direction.

21. The disposable wearable absorbent article of claim 1, wherein the outer edge of each of the first and second side panels is folded over towards the chassis such that the mechanical fastening material fastens to a surface of the each of the first and second side panels.

22. The disposable wearable absorbent article according to claim 1, wherein each of the first and second side panels has a height $H_2$ at a chassis end in the range of: from 100 mm to 240 mm.

23. The disposable wearable absorbent article according to claim 22, wherein the outer edge of each of the first and second side panels has a gathered height $H_1$ between 50% and 95% of the height $H_2$.

24. The disposable wearable absorbent article according to claim 1, wherein each of the gathered first and second side panels is formed from a flat sheet having an ungathered height $H_3$ at an outer edge of the flat sheet, and wherein a gathered height $H_1$ of the outer edge of the each of the gathered first and second side panels is from 50 to 95% of the ungathered height $H_3$.

25. The disposable wearable absorbent article according to claim 1, further comprising:
    a third side panel extending transversally outwards from a first lateral side of the front region of the chassis towards a third outer edge; and
    a fourth side panel extending transversally outwards from a second lateral side of the front region of the chassis towards a fourth outer edge,
    wherein the mechanical fastening material on the first and second side panels is configured to engage the front region of the chassis or the third and fourth side panels respectively, whereby the first and second side panels are coupled to the front region of the chassis.

26. The disposable wearable absorbent article according to claim 1, wherein the mechanical fastening material comprises a hook patch.

27. A method of manufacturing a disposable wearable absorbent article comprising a chassis and first and second side panels respectively extending transversely in first and second lateral directions, the method comprising the steps of:
    (i) providing a chassis extending in a longitudinal direction and having a front region, a rear region and a central region disposed in the longitudinal direction between the front region and the rear region;
    (ii) affixing the first side panel to the chassis such that the first side panel extends transversally outwards in the first lateral direction towards a first panel outer edge;
    (iii) affixing the second side panel to the chassis such that the second side panel extends transversally outwards in a second lateral direction towards a second panel outer edge;
    (iv) gathering a free end portion of each of the first and second side panels, adjacent the outer edge thereof, in the longitudinal direction to form at least one pleat extending in the transverse direction.

28. The method according to claim 27, wherein the step of gathering the free end portion of the each of the first and second side panels comprises the steps of:
    (v) extending a first length of elastic binding material in the longitudinal direction to an extended configuration and securing the elastic material, in the extended configuration, at the outer edge of the first side panel in the longitudinal direction;
    (vi) extending a second length of elastic material in the longitudinal direction to an extended configuration and securing the elastic material, in the extended configuration, at the outer edge of the second side panel in the longitudinal direction;
    (vii) relaxing the elastic material to gather each of the first and second side panels in the longitudinal direction.

29. The method according to claim 27, wherein the step of gathering the free end portion of the each of the first and second side panels comprises the steps of:
    gathering the outer edge of each of the first and second side panels;
    applying a binding material to the free end portion of the each of the first and second side panels to maintain the each of the first and second side panels in a gathered configuration.

30. The method according to claim 27, wherein the method further comprises affixing a mechanical fastening material to the outer edge of each of the first and second side panels:
    before the step (vi); or
    after the step (vi); or
    at the same time as the step (vi).

31. The method according to claim 30, wherein the binding material comprises the mechanical fastening material.

32. The method according to claim 27, further comprising the step of folding the outer edge of each of the first and second side panels over towards the chassis to temporarily fasten the mechanical fastening material to a gathered surface of the each of the first and second side panels.

33. The method according to claim 27, wherein at least one of the first and second side panels is formed of a rectangular sheet of material.

* * * * *